United States Patent [19]

Shaw

[11] Patent Number: 4,949,717
[45] Date of Patent: Aug. 21, 1990

[54] SURGICAL INSTRUMENT WITH SUTURE CUTTER

[76] Inventor: Edward L. Shaw, 5615 N. Palacio Way, Phoenix, Ariz. 85014

[21] Appl. No.: 169,418

[22] Filed: Mar. 17, 1988

[51] Int. Cl.[5] .............................................. A61B 17/06
[52] U.S. Cl. ..................................... 606/147; 606/174
[58] Field of Search ............... 128/321, 340, 318, 322, 128/305; 81/415, 417, 418, 420, 421

[56] References Cited

U.S. PATENT DOCUMENTS

| Re. 22,857 | 3/1947 | Ogburn | 128/340 |
|---|---|---|---|
| 1,579,379 | 4/1926 | Marbel | 128/340 |
| 1,876,792 | 9/1932 | Thompson | 128/340 |
| 2,315,326 | 3/1943 | Gmeiner | 128/340 |
| 2,394,807 | 2/1946 | Robinson | 81/415 |
| 2,652,832 | 9/1953 | Castroviejo | 128/340 |
| 2,885,781 | 5/1959 | Bauer | 81/417 |
| 3,166,071 | 1/1965 | Mayer | 128/318 |
| 3,443,313 | 5/1969 | Profy | 128/318 |
| 3,577,991 | 5/1971 | Wilkinson | 128/340 |
| 3,763,860 | 10/1973 | Clarke | 128/340 |
| 3,786,815 | 1/1974 | Ericson | 128/321 |
| 3,805,792 | 4/1974 | Cogley | 128/346 |
| 3,921,478 | 11/1975 | Ygfors | 81/417 |
| 4,165,745 | 8/1979 | Heifetz | 128/321 |
| 4,375,218 | 3/1983 | DiGeronimo | 128/321 |
| 4,392,494 | 7/1983 | Ashby | 128/321 |
| 4,446,866 | 5/1984 | Davison | 128/340 |
| 4,478,221 | 10/1984 | Heiss | 128/340 |

FOREIGN PATENT DOCUMENTS 529919 12/1921 France .................. 128/322

Primary Examiner—Edward M. Coven
Assistant Examiner—Gary Jackson

[57] ABSTRACT

A cross-action surgical instrument has a pair of opposed jaws providing the capacity for clampingly receiving and holding a suturing needle, and severing a suture when stitching is complete. A stop member is formed on one of the opposed jaws extending toward and past the second of said jaws to prevent the suturing needle or the suture from reaching the pivot between the first and second jaws. The stop member registers with a groove formed in the remaining jaw and the uppermost edge of the groove has a honed edge against which the suture is sheared by the stop member when the first and second jaws are closed, or forced together.

9 Claims, 2 Drawing Sheets

SURGICAL INSTRUMENT WITH SUTURE CUTTER

The present invention relates generally to surgical instruments and, more particularly, to combining a suture cutter with certain cross-action surgical instruments.

BACKGROUND OF THE INVENTION

Surgery requires the use of surgical instruments within a restricted and unusually sensitive operating field. During surgery, the field becomes crowded if a large number of surgical instruments must be used simultaneously, with concomitant difficulty for the surgical team to maintain a clear viewing area. Under such circumstances, surgical instruments designed to perform more than one task are of particular usefulness.

One technique used extensively in surgery is the placement of sutures, or stitches, to close a wound or incision. Such sutures are usually applied by attaching surgical thread to a curved needle and manipulating the needle through the tissue at the edges of the wound or incision and thereafter drawing the surgical thread tightly to bring the edges of the wound or incision together to facilitate the healing process. Thereafter, the surgical thread is knotted and severed, leaving behind only that much surgical thread required to firmly close the wound.

Because the thread and the needle are necessarily of an extremely small size, it is common for surgeons to use a needle holder, that is, a surgical instrument having an easily gripped and manipulable handle and a pair of cross-action, or scissors-like jaws within which the surgical needle is firmly clamped. The instrument is then manipulated to pierce the tissue with the needle, draw the needle through the tissue and position it for another stroke. After the stitching procedure has been completed, the needle is removed and the thread is knotted, often times by drawing the thread over the needle holder itself to form the knot.

Heretofore, it has been common for a surgeon to use a separate cutting instrument to sever the suture after knotting has been completed. This often times calls for the use of a second person to perform the severing operation or, at the very least, requires the surgeon acting alone to be ambidexterous or unusually well-coordinated to draw the suture taut with the needle holder and sever the suture with a separate cutting instrument. At the very least, the surgeon may be required to put down the needle holder, pick up a cutting instrument to sever the suture, and pick up the needle holder again to begin the next stitch.

Attempts have been made in the past to combine suture-severing and other functions on a single surgical instrument. Exemplary of such prior efforts is U.S. Pat. No. 2,315,326 (Gmeiner), which teaches a surgical instrument having a serrated jaw within which a suturing needle is clamped, a stop block against which the needle abuts, and a cutting edge formed on the jaws behind the stop block. After suturing is completed, the jaws are unlocked to release the needle and the thread is thereafter drawn past the stop block into that portion of the jaws upon which the cutting edge is formed. The suture is then severed.

In U.S. Pat. No. 4,271,838 (Lasner. et al.), a suture cutter is disclosed having a pair of clamping jaws for the needle, a stop block having a cutting edge formed thereon, and a jaw portion over which the stop block is passed to sever a stuture positioned between the jaw portion and the stop block cutting edge.

Another problem to be faced when using a cross-action surgical instrument for the severing of a suture is the tendency of the suture to snag in the joint formed by the hinging together of the instrument's opposed jaws. U.S. Pat. No. 2,726,657 (Tabrah) discloses a snag preventer on a surgical instrument wherein the exposed edges which may effectively snag the suture are beveled or rounded in order to minimize the possibility of such snags. U.S. Pat. No. 3,577,991 (Wilkinson) teaches a forceps having an external covering shield positioned proximate the jaws to prevent snags.

It should be noted that the snagging may occur during the severing operation or during the knotting operation wherein a loop of the suture is commonly drawn over the jaws of the suturing instruments.

Other examples of combined surgical instruments and cutting surfaces also exist. U.S. Pat. No. 4,478,221 (Heiss) teaches and describes a clamp having a slidable cutter which is withdrawn into the instrument when not in use. U.S. Pat. No. Re. 22,857 (Ogburn) teaches a suturing instrument with a pair of jaws used for holding a suturing needle and a suture cutter positioned along the lowermost leg of the suturing instrument.

U.S. Pat. No. 3,443,313 (Profy) teaches a hemostat having separate clamping tips and cutting tips formed proximate each other, with an externally positioned blade along one side of the cutting tip for severing a suture. The clamping tip is then used to remove the suture.

U.S. Pat. No. 1,579,379 (Marbel) demonstrates the use of a surgical instrument having a forward jaw portion used for clamping and a rearward jaw portion used for severing with no stop member therebetween to act as a stop for the suture or as a clamping site for the needle.

U.S. Pat. No. 1,876,792 (Thompson) teaches a clamp having a pair of cutting jaws mounted on the clamping surface. The clamping and cutting jaws are used separately.

U.S. Pat. No. 3,763,860 (Clarke) teaches a laparoscopic instrument having a forward clamping jaw behind which a cutting edge is positioned.

In U.S. Pat. No. 3,840,817 (Violante), a suturing instrument is disclosed which uses a sharpened edge formed on the needle protector to act as a site for severing the suture. A similar teaching is found in U.S. Pat. No. 4,224,947 (Fukuda) wherein an aperture in the needle, through which the suturing thread is drawn, has a sharpened edge against which the suture may be pulled and severed.

U.S. Pat. No. 4,452,246 (Bader, et al.) and corresponding EPO patent No. WO83/00994 teach a surgical instrument having three jaws, one of which has a cutting edge formed thereon and which may be separately moved against a suture held between the remaining two jaws in order to sever the suture.

U.S. Pat. No. 4,375,218 (DiGeronimo) teaches a forceps having mounted thereon a retractable scalpel used for converting the tool from a forceps to a scalpel and vice versa.

There is a need for surgical instruments, such as forceps or needle-holders having suture-severing capabilities manufactured in a compact, uncomplicated device without extra handles, extra cutting elements, extra blades and the like. There is also a need for such instruments to minimize the snagging of the sutures on the instrument. There is a further need to have such an instrument manufactured in a size useful for delicate surgical procedures.

A particular form of surgery requiring extremely delicately carried-out surgical procedures is ophthalmic surgery. Ophthalmic surgery, with its relatively small operating field, and its delicate and vulnerable tissue structures, demands a great deal of dexterity and control on the part of a surgeon. Under such conditions, the use of multiple-function instruments increases the surgeon's effectiveness by requiring fewer instruments to carry out and complete such procedures as suturing.

BRIEF DESCRIPTION OF THE DRAWINGS

These and further objects will become more apparent upon review of the accompanying drawings wherein.

DETAILED DESCRIPTION OF THE INVENTION

Figure 1:
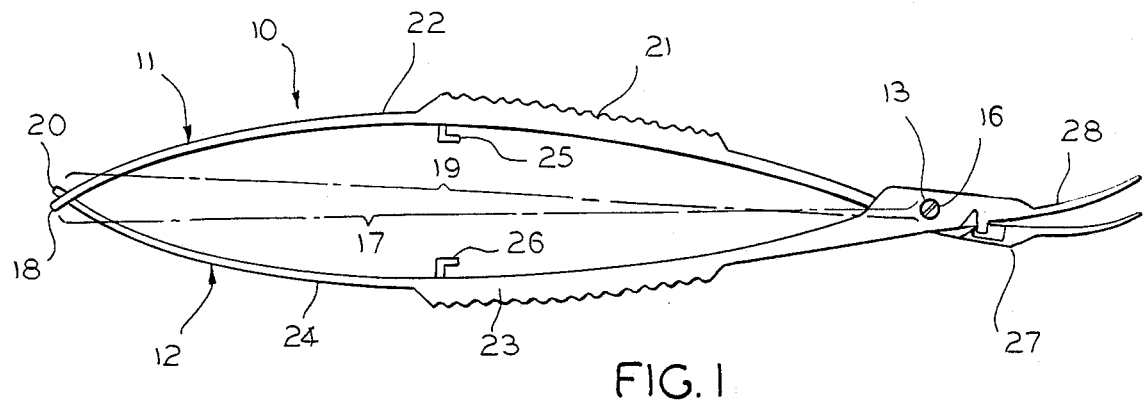
FIG. 1 is a side elevation view of a preferred embodiment of the present invention shown in an open position.
Figure 5:
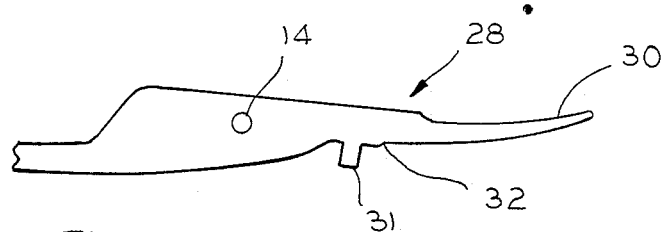
FIG. 5 is a side elevation of the upper jaw shown in FIG. 3.

Referring now to FIG. 1, the numeral 10 indicates generally a cross-action type of surgical instrument intended for use as a needle holder/suture cutter. As shown in the preferred embodiment in FIG. 1, instrument 10 has an upper arm 11 and a lower arm 12 joined together at a pivot 13. As shown, pivot 13 preferably comprises a screw aperture 14 as seen in FIG. 5 and a tapped aperture 14 and is screwed into tapped aperture 15 to secure upper arm 11 and lower arm 12 together.

Upper arm 11 includes a handle segment 17 generally described as extending from end 18 of arm 11 to pivot 13. In like fashion, lower arm 12 has a handle segment 19 extending from lower arm end 20 to proximate pivot 13.

Figure 2:
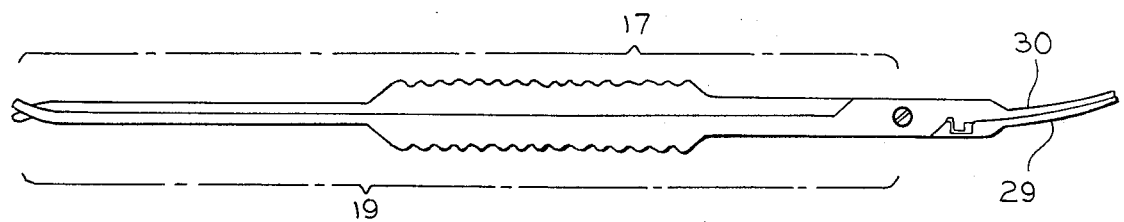
FIG. 2 is a side elevation view of the device of FIG. 1 shown in the closed or locked position.

Each such handle segment 17, 19 has, respectively, a hand grip 21, 23 and, respectively, spring segments and 22 and 24. In the preferred embodiment of instrument 10, hand grips 21 and 23 are formed as relatively thickened and rigid segments, while spring segments 22 and 24 are formed as relatively thinner, flexible and resilient segments. As shown in FIGS. 1 and 2, spring segments 22 and 24 are interengaged proximate ends 18 and 20 and thus create a biasing or resilient force which, in the at-rest position, forces hand segments 17 and 19 apart from one another. In order to maintain instrument 10 in a closed or locked position, retaining catches 25 and 26 are formed on the inner surfaces of hand grip segments 21 and 23. When hand grip segments 21 and 23 are gripped and forced to the closed position, catches 25 and 26 can be interengaged to hold instrument 10 in the closed position demonstrated in FIG. 2.

Figure 3:
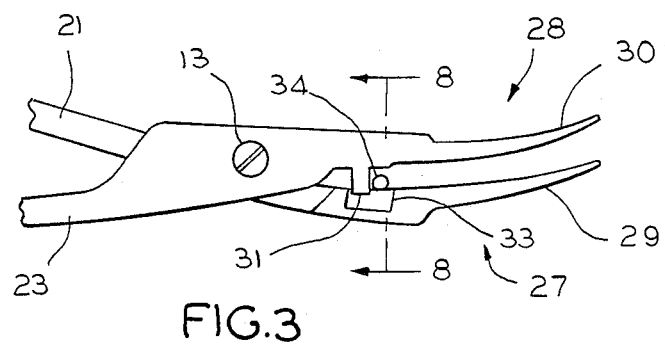
FIG. 3 is an enlarged side elevation of the jaws of the instrument shown in FIG. 1, with the jaws in the open position.

Referring now to FIGS. 1 and 3, it may be seen that handle segment 21 terminates in a lower jaw segment 27. As is typical with surgical instruments used for clamping or gripping, lower jaw segment 27 includes a slender, protruding jaw 29 while upper jaw segment 28 includes a similarly formed upper jaw 30. As best seen in FIG. 2, when instrument 10 is in its closed position, jaws 29 and 30 are clamped tightly together, and a needle held therebetween will be clenched firmly.

Referring now to FIG. 5, it may be seen that upper jaw 30 has formed thereon a stop block 31 extending downwardly from jaw 30 toward lower jaw segment 27. Stop block 31 includes a generally ramped guide 32 extending from jaw 30 to stop block 31.

Figure 4:
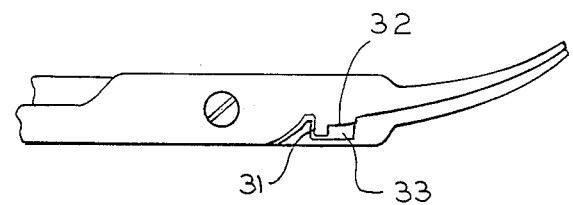
FIG. 4 is a front view of the jaws shown in FIG. 3 in the closed position.
Figure 6:
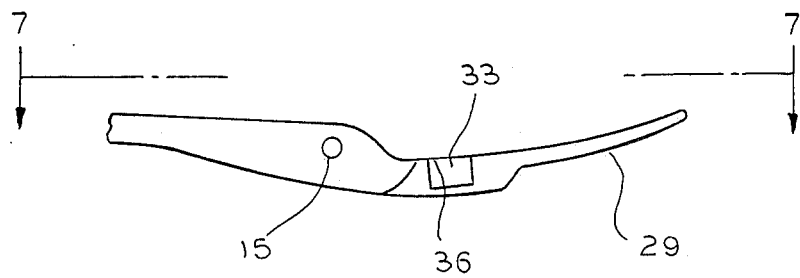
FIG. 6 is a side elevation of the lower jaw shown in FIG. 6.

As best seen in FIGS. 3 and 6, lower jaw segment 27 has a cut-out or groove 33 formed thereon along the innermost lateral surface thereof. Groove 33 registers with and receives stop block 31 and guide block 32 when instrument 10 is in the fully closed position, as best shown in FIG. 4. The positioning and formation of groove 33 is also illustrated in FIG. 7.

Figure 7:
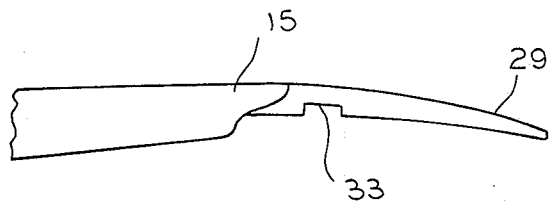
FIG. 7 is a partial sectional view of the jaw shown in FIG. 6, taken along lines 7—7.
Figure 8:
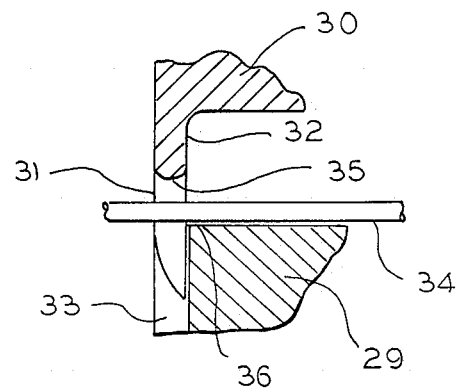
FIG. 8 is a partial sectional view of the jaw shown in FIG. 3, taken along lines 8—8.

Referring now to FIGS. 3 and 7, instrument 10 is shown with jaws 29 and 30 open to receive suture 34. As seen in FIG. 3 stop block 31 prevents suture 34 from snagging at the pivot point where upper and lower jaw segments 28 and 27 "scissor" together. In like fashion, stop block 31 will prevent a suturing needle from inadvertently slipping backward into the joint formed by upper and lower jaw segments 28 and 27 and thereby prevent such needle from "jamming" the joint.

Cooperating features of upper and lower jaws 30 and 29 provide a site for severing suture 34 as desired. As shown in FIG. 7, when suture 34 is positioned to rest against stop block 31, it is directly beneath lower surface 35 of guide 32. A honed cutting edge 36 is formed as the uppermost edge of pocket 33. As instrument 10 is closed, stop 31 and guide 32 enter pocket 33 causing lower guide surface 35 to contact suture 34 and shear suture 34 against honed edge 36 of pocket 33. With honed edge 36 positioned ahead of stop block 31, suture 34 does not reach the joint formed by upper and lower jaw members 28 and 27 and thereby become entangled or break prematurely.

Use of the present invention may be described as follows. Catches 25 and 26 are disengaged to allow spring segments 11 and 12 to open jaw segments 27 and 28. Instrument 10 is then grasped at the handle portions 21 and 23, and jaws 29 and 30 are clasped about a suturing needle. After the suturing needle has been used to pierce the edges of the tissue to be sutured, and the suture has been knotted, instrument 10 is guided to position suture 34 against stop block 31, whereupon instrument 10 is closed. Upon closure, lowermost guide surface 35 contacts suture 34 and shears it against honed edge 36.

It is expected that manufacture of instrument 10 will involve the use of high grade surgical stainless steel and it is also anticipated that the suture retaining/severing features of the present invention may be included on cross-action surgical instruments bearing other configurations as well.

It is also anticipated that at least a portion of stop block 31 will remain within pocket 33 throught the usable range of motion of jaw segments 27 and 28 to prevent the inadvertent snagging of a suture at the instrument's pivot point. When instrument 10 is fully closed, stop block 31 is flush with, or does not protrude past lower jaw segment 28, thereby protecting surrounding tissue from contact with stop block 31 when, for example, severing suture 34.

Positioning honed edge 36 at a lateral edge of instrument 10 (as seen in FIG. 7) enables instrument 10 to shear close to where the suture knot is formed.

It is also to be understood that, in the foregoing examples, each arm-and-jaw assembly is formed as an intergal and unitary piece, with the two such pieces joined together at pivot 13 to form a completed instrument.

While the foregoing has presented certain specific embodiments of the present invention, it is to be understood that there embodiments have been presented by way of example only. It is expected that others skilled in the art will perceive variations which, while differing from the foregoing, do not depart from the spirit and scope of the invention as herein described and claimed, and no limitations on the invention are herein intended.

What is claimed is:

1. In a hand-manipulable cross-action surgical instrument, said instrument of the type having opposed first and second members, each said member having a pivot portion, a jaw extending in a first direction from said pivot portion, and a handle portion extending in a second direction opposite that of said first direction, said first and second members pivotably joined at said pivot portion, said handle portions adapted to scissor said jaws together from an open position to progressively overlap portions of said jaws from said pivot portion toward a closed position to clamping receive either a first severable object or a second, non-severable object therebetween, the improvement comprising:

first means formed on said jaws to stop said first or second object from reaching the point at which said first and second jaws are overlapped; and
   second means formed on said jaws to selectively sever said first object,
   said severing means being positioned proximate to and in front of said stop means.

2. The apparatus as recited in claim 1 wherein said stop means includes a stop member positioned on said first of said jaws and extending in a direction toward and extending past said second of said jaws throughout the normal range of motion of said instrument between said open position and said closed position.

3. The apparatus as recited in claim 2 wherein said stop means further includes a groove formed on said second jaw,
   said stop means registering with said groove when said instrument is moved toward said closed position.

4. The apparatus as recited in claim 1 wherein said severing means includes a honed edge formed on said second jaw,
   said honed edge positioned forward of and proximate to said stop means when said instrument is in said closed position;
   said honed edge and said second jaw contacting said first object at said stop means to impart to said first object a shearing force of sufficient strength to sever said first object.

5. The apparatus as recited in claim 1 wherein said stop means includes a stop member extending from said first jaw toward said second jaw,
   said stop member extending past and overlapping said second jaw when said instrument is in said open position;
   a groove formed on said second jaw with which said stop member registers when said instrument is in said closed position; and
   said severing means includes a honed edge formed on said second jaw at said groove whereby said first object, when positioned against said stop member, is urged by said first jaw into shearing contact with said honed edge when said instrument is moved to said closed position.

6. The apparatus as recited in claim 5 wherein said severing means further includes a shoulder formed on said first jaw,
   said shoulder extending forward of and formed integrally with said stop member,
   said shoulder contacting said first object and pressing said first object shearingly against said honed edge when said instrument is moved toward said closed position.

7. The apparatus as recited in claim 5 wherein said stop member does not extend past said groove when said instrument is in said closed position.

8. The apparatus as recited in claim 1 wherein said surgical instrument is a needle holder.

9. The apparatus as recited in claim 1 wherein said surgical instrument is a forceps.

* * * * *